(12) United States Patent
Giuntoli et al.

(10) Patent No.: US 7,983,761 B2
(45) Date of Patent: *Jul. 19, 2011

(54) ELECTRO-ACUPUNCTURE DEVICE WITH COMPRESSIBLE GASKET

(75) Inventors: David M. Giuntoli, Carlsbad, CA (US); Gregory J. Gruzdowich, Carlsbad, CA (US); Thomas L. Grey, Carlsbad, CA (US)

(73) Assignee: Relief Band Medical Technologies LLC, Chicago, IL (US)

( * ) Notice: Subject to any disclaimer, the term of this patent is extended or adjusted under 35 U.S.C. 154(b) by 341 days.

This patent is subject to a terminal disclaimer.

(21) Appl. No.: 11/941,724

(22) Filed: Nov. 16, 2007

(65) Prior Publication Data

US 2008/0071329 A1  Mar. 20, 2008

Related U.S. Application Data

(63) Continuation of application No. 10/796,391, filed on Mar. 9, 2004, now abandoned, which is a continuation of application No. 09/896,968, filed on Jun. 29, 2001, now Pat. No. 6,735,480.

(51) Int. Cl.
*A61N 1/18* (2006.01)

(52) U.S. Cl. ............... 607/72; 607/44; 600/554

(58) Field of Classification Search ............ 600/554; 607/44
See application file for complete search history.

(56) References Cited

U.S. PATENT DOCUMENTS

| | | | |
|---|---|---|---|
| 4,524,775 A * | 6/1985 | Rasmussen | 600/391 |
| 4,981,146 A | 1/1991 | Bertolucci | |
| 4,982,742 A | 1/1991 | Claude | |
| 5,085,217 A | 2/1992 | Shimizu | |
| D337,642 S | 7/1993 | Yamasaki et al. | |
| 5,314,423 A | 5/1994 | Seney | |
| 5,520,683 A * | 5/1996 | Subramaniam et al. | 606/32 |
| 6,178,352 B1 * | 1/2001 | Gruzdowich et al. | 607/44 |

* cited by examiner

*Primary Examiner* — Niketa I Patel
*Assistant Examiner* — Rex Holmes
(74) *Attorney, Agent, or Firm* — Marina N. Saito; Loeb & Loeb, LLP

(57) ABSTRACT

An electro-acupuncture device for controlling nausea. The device includes a wristwatch like housing, circuitry for generating electro-acupuncture stimulus disposed within the housing, and a strap for securing the housing to the wrist. The device also includes a pair of D-shaped electrodes disposed on the bottom outer surface of the housing. A gasket made of an electrically non-conductive material is applied to the bottom outer surface of the housing. The gasket has apertures which are sized and shaped to receive the D-shaped electrodes. When the device is strapped to a patient's wrist, the electrodes contact the wrist and provide electric stimulation to the wrist.

17 Claims, 4 Drawing Sheets

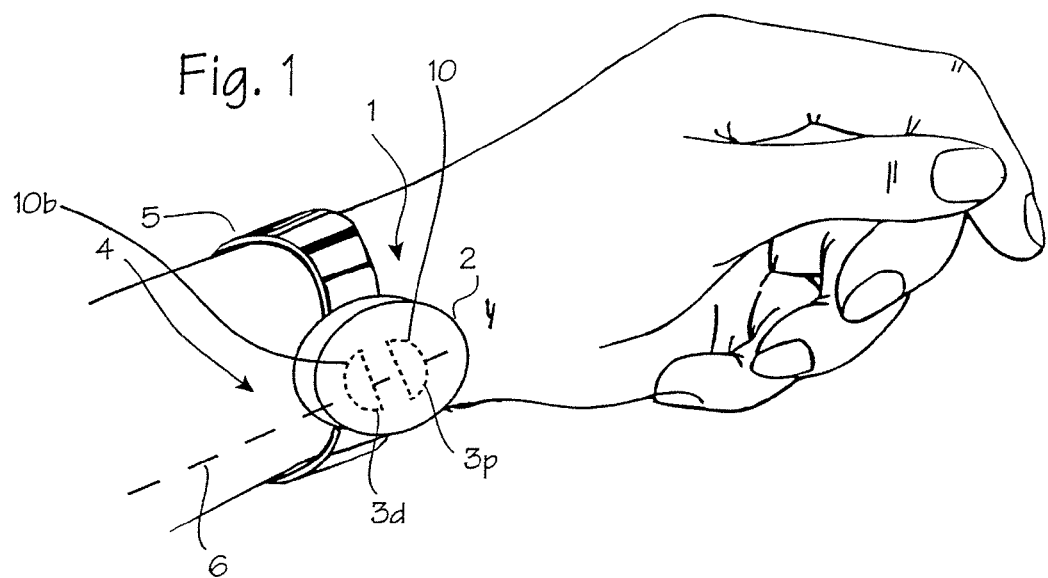
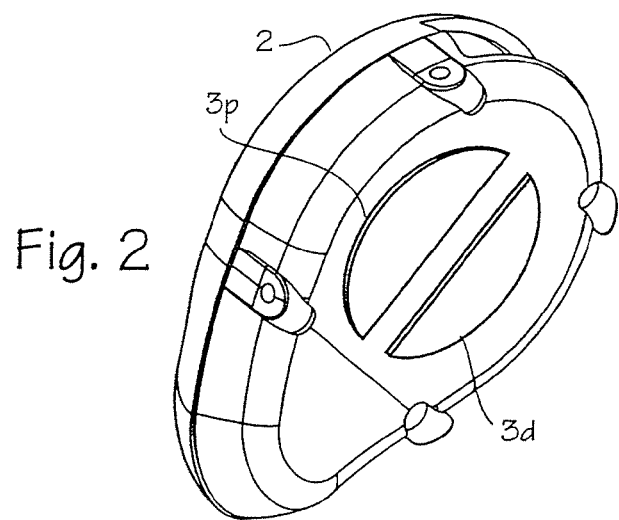

ELECTRO-ACUPUNCTURE DEVICE WITH COMPRESSIBLE GASKET

CROSS-REFERENCE TO RELATED APPLICATIONS

This application is a continuation of co-pending U.S. patent application Ser. No. 10/796,391 filed Mar. 9, 2004, which is a continuation of application Ser. No. 09/896,968 filed Jun. 29, 2001, now U.S. Pat. No. 6,735,480, issued May 11, 2004, the entire contents of all are incorporated herein by reference.

FIELD OF THE INVENTIONS

The devices described below relate to the field of electro-acupuncture and non-invasive stimulation of nerves.

BACKGROUND OF THE INVENTIONS

We have developed an electro-acupuncture or nerve stimulation device which has proven effective for the control of nausea and vomiting. The basic device is described in Bertolucci, *Nausea Control Device,* U.S. Pat. No. 4,981,146 (Jan. 1, 1991). The device, marketed under the trademark Relief-Band®, is worn on the wrist like a wristwatch, with a watch-like housing which is positioned on the underside of the wrist. The housing has two electrodes on the inside face (the face in contact with the wrist when secured to the wrist), a battery and circuitry inside the housing, and control buttons on the outer face. A patient suffering from nausea or vomiting (from motion sickness, morning sickness, chemotherapy, or anesthesia) can strap the device onto their wrist and turn it on. When turned on, the device emits an electrical stimulation pulse over the P6 acupuncture point (corresponding to the superficial course of the meridian nerve through the wrist). Within several minutes, most patients experience a substantial relief of nausea. The device uses non-invasive nerve stimulation whereby electricity is passed through the electrodes to stimulate nerves located on the ventral side of the wrist (this anatomical position is sometimes referred to as the palmar side of the wrist). The treatment provided by the device is sometimes referred to as electro-acupuncture, which is a form of acupuncture, and the ventral site of application is referred to in the acupuncture art as the P6 point, pericardium 6 point, or master point of the pericardium meridian (sometimes referred to as the vascular meridian). It is also portable, self-contained and convenient to the patient. Electrical pulse repetition rate of approximately 70 pulses per second a pulse width of 80 microseconds have been found to provide effective relief of nausea in a patient. Our currently preferred electrical pulse pattern comprises about 350 microsecond pulse width at about 31 pulses per second at power levels of about 10-35 milliamps peak pulse height. Thus a wide range of pulse patterns may be used in non-invasive nerve stimulation devices.

In each of our electro-acupuncture products, the stimulation and effect are greatly enhanced if the patient applies a gel to the skin before strapping the device onto the wrist. This gel serves as an electronic to ionic current conversion layer between the electrodes and the dry outer skin layer. This electrical conduction layer, sometimes referred to as an impedance matching layer, greatly enhances the effect of the device and lowers the power requirements for the device. The patient applies the gel to the skin before strapping the device onto the wrist. The gel may be referred to as a conductivity gel or an electro-medical coupling agent. The users may use too much gel, too little gel, or apply it too infrequently. Some users may omit application of the gel, either through forgetfulness or ignorance of need to use it. Additionally, gel may be removed by water in the environment of use, such as where the device is used for seasickness on a small sail boat while the user is operating the sail boat.

SUMMARY

The devices and methods described below provide a nerve stimulation or electro-acupuncture device which may be used without the application of conductivity gel, or with minimal application of conductivity gel. The nerve stimulation device comprises a housing preferably shaped like a wristwatch that can be strapped to a patient's wrist about the P6 acupuncture point. The housing houses the control circuitry and a battery. The nerve stimulation device includes two D-shaped electrodes connected to control circuitry and the battery. The pair of electrodes is mounted to the inner face of the housing, so that they rest over the P6 acupuncture point when the housing is worn on the patient's wrist. The D-shaped electrodes effectively provide stimulation to the patient without the need for additional application of conductivity gel or impedance matching material. The nerve stimulation device also comprises a gasket made of an electrically non-conductive material such as neoprene or silicone. The gasket includes two apertures sized and shaped to receive the electrodes when the gasket is applied to the device. The gasket provides electrical insulation between the electrodes so as to prevent a short circuit between the electrodes. The gasket also acts as a seal between the electrodes and the patient's wrist to seal in conductivity gel or other conductive material. It will also serve to retain perspiration in amounts sufficient that the perspiration itself serves as the conductive material.

BRIEF DESCRIPTION OF THE DRAWINGS

FIG. 1 is a view of the nerve stimulation device in use on the wrist of a patient.

FIG. 2 is a perspective view of the bottom of the nerve stimulation device.

DETAILED DESCRIPTION OF THE INVENTIONS

Figure 3:
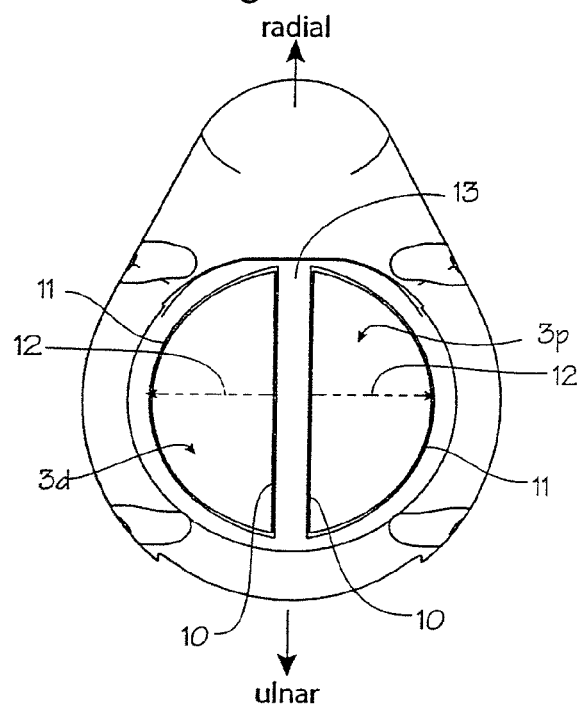
FIG. 3 is a bottom view of the nerve stimulation device.

FIG. 1 illustrates an electro-acupuncture or non-invasive nerve stimulation device 1 in use on the wrist of a patient. The basic nerve stimulation device is described in Bertolucci, Nausea Control Device, U.S. Pat. No. 4,981,146 (Jan. 1, 1991), which is incorporated herein in its entirety. FIG. 2 is a perspective view of the underside of the nerve-stimulation device 1. The nerve-stimulation device is comprised of a housing 2. The required battery, therapeutic pulse generator, and control electronics are housed within the housing, and input mechanisms (push buttons, dials, and the like) are located on the outer face of the housing. The stimulation device is further comprised of a pair of electrodes 3*d* and 3*p* attached to the bottom outer surface of the housing. The nerve stimulation device is secured to the ventral side of the wrist 4 with a strap 5 such that the pair of electrodes is disposed over the median nerve 6 (indicated by the phantom line shown in FIG. 1) and in contact with the skin in the vicinity of the P6 acupuncture point. Relative to the wrist, electrode 3d is a distal electrode, located distally of proximal electrode 3p, so that the electrodes are arranged along the medial nerve, with their major axes being perpendicular to the median nerve (that is, perpendicular to the length of the arm). The electrodes are operably connected to the pulse generator within the housing. During operation, the pulse generator provides electrical stimulation pulses to the electrodes, and these pulses are transmitted through the patient's skin to underlying nerves. The strap 5 can be provided in the form of a typical non-elastic watchband, a watchband which includes a segment of elastic material, or it may be comprised of elastic hook and loop fastener material.

Figure 4:
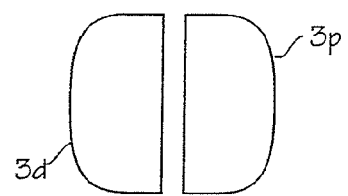
FIG. 4 illustrates alternative shapes for the electrodes.

FIG. 3 is a bottom view of the nerve stimulation device 1. The electrodes 3 each have a "D" or semi-circular shape such that the electrodes define straight edges 10 and radial or arcuate edges 11, and are arranged with the straight edges facing each other in apposition. The electrodes have a radius 12 of about 0.5 inches, but may be provided in sizes ranging from 0.25 inches to 1.5 inches (about 0.75 to 4 cm). This radius corresponds to the radius of the arcuate edge in the case where the electrodes are D-shaped, as shown. The electrodes may be more rectangular, as shown in FIG. 4, each with a width of about 0.5 inches (13 mm) and any radius of curvature which will fit on the chosen housing. The long axis of the electrodes (corresponding to the straight edge 10 of the electrodes, and lying transverse to the wrist during use) may be limited in size in order to conform to the local anatomy of the wrist, so that it may span the median nerve and the P-6 point without also overlying nearby acupuncture points such as the L-7 (Lieque) point or the He 7 (Shenmen) point. The distal to proximal width of the electrode array is limited in size so that the electrodes span a suitable length of the superficial course of the median nerve and overlie the P6 point, but do not overlie more distal and proximal acupuncture points such as the P7 and P5 points (located on the crease of the wrist and about two inches proximal to the crease, respectively). The size of the housing is determined by the need to fit comfortably on the wrist, allow free extension and flexion of the wrist, and concentrate stimulation over the P-6 acupuncture point. The electrodes are separated from each other such that there is an inter-electrode gap 13 along the opposing straight edges of the electrodes. The inter-electrode gap separates the electrodes to prevent a short circuit between the electrodes and force current flow between the electrodes to flow through the body. The inter-electrode gap is approximately 0.14 inches wide (3-5 mm), and may range from 0.05 to 0.5 (1-15 mm) in width. The electrodes can be manufactured to the appropriate size and shape by stamping, wherein a sheet of suitable metal is stamped by a die having the electrode shape.

The dimensions of our D-shaped electrodes 3 have enhanced the effectiveness of the nerve stimulation device. The D-shape electrodes are relatively larger in surface area than conventional electrodes, such as those provided in our prior devices (which were rounded rectangular, or hot-dog shaped, with dimensions of about 0.75 inches by 0.2 inches (19 by 5 mm)). When an equivalent electric current is supplied to the D-shaped electrode and the smaller conventional electrodes, a lower current density is expected in the larger D-shaped electrodes. A lower current density should result in less effective nerve stimulation with our currently preferred power level (about 10-35 milliamps peak pulse height). However, we observed substantially improved current density and nerve stimulation with the large D-shaped electrodes vis-à-vis the conventional electrodes. Thus, the D-shaped electrodes have a larger surface area than the smaller conventional electrodes but provide improved current density and improved nerve stimulation. The improvement is sufficient to allow use of these electrodes without a conductivity gel, or, concomitantly, use of the electrodes with conductivity gel but with much lower applied power. It is not necessary to increase the power level to the D-shape electrodes to maintain our desired current density. Furthermore, we found that the D-shaped electrodes provide sufficient nerve stimulation without the need for a conductive gel.

In use, the user straps the device onto the wrist so that the electrodes overlie the P6 acupuncture point. Prior to applying the device to the wrist, the user need not apply conductivity gel. When applied to the wrist oriented as indicated by the arrows, with one end on the ulnar side (lateral side, which is typically farthest from the body) of the wrist and the other end on the radial side (medial side which is closest to the body or the thumb) of the wrist, the electrodes are arranged proximally and distally on the wrist. The electronics within the housing are activated by the user, and are programmed to generate an electrical pulse pattern with a 350 microsecond pulse width at about 31 pulses per second at power levels of about 10-35 milliamps peak pulse height. This pulse pattern is effective to create an electro-acupuncture effect on the nerve, but other pulse patterns may also be effective. The user will feel the same effect as application of the same stimulus through oblong electrodes and conductivity gel. Additionally, the user may apply gel, and the device may be programmed to generate pulses at lower power levels to achieve a similar level of stimulation while reducing battery consumption. The user need not be overly precise regarding the placement of the electrodes over the wrist, as the D-shaped electrodes are much less position sensitive than the conventional electrodes used in our prior devices. That is, small variations in the longitudinal and transverse location of the electrodes relative to the P6 point and the superficial course of the median nerve in the wrist do not negatively affect the transmission of electrical stimulus from the electrodes to the median nerve.

Figure 5:
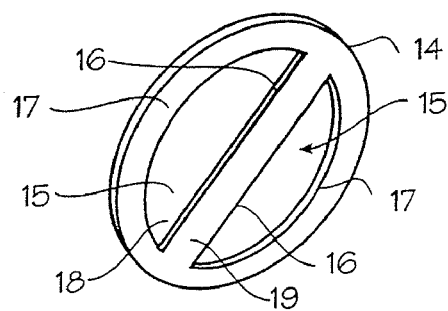
FIG. 5 is a perspective view of a gasket adapted for use with the nerve stimulation device.

Additionally, we found that the patient's own perspiration can provide a sufficient conduction layer or impedance matching layer between the electrodes and the skin, especially when used in conjunction with a sealing gasket around the electrodes. FIG. 5 is a perspective view of a gasket 14 adapted for use with the nerve stimulation device 1 of FIG. 2. The gasket comprises two apertures 15, wherein the apertures are sized and oriented to receive the D-shaped electrodes 3. The apertures have D-shapes with straight edges 16 and radial edges 17. The gasket has a uniform gasket thickness 18 about the aperture edges. The gasket also includes an electrode-separating member 19 defined by the gasket material disposed along the straight edges of the apertures. The electrode-separating member is sized such that when the gasket is attached to the nerve stimulation device, the electrode-separating member fits snugly in the inter-electrode gap 13. The gasket can be made from any suitable dielectric or electrical insulating material such as neoprene, silicone, urethane, rubber or other materials.

Figure 6:
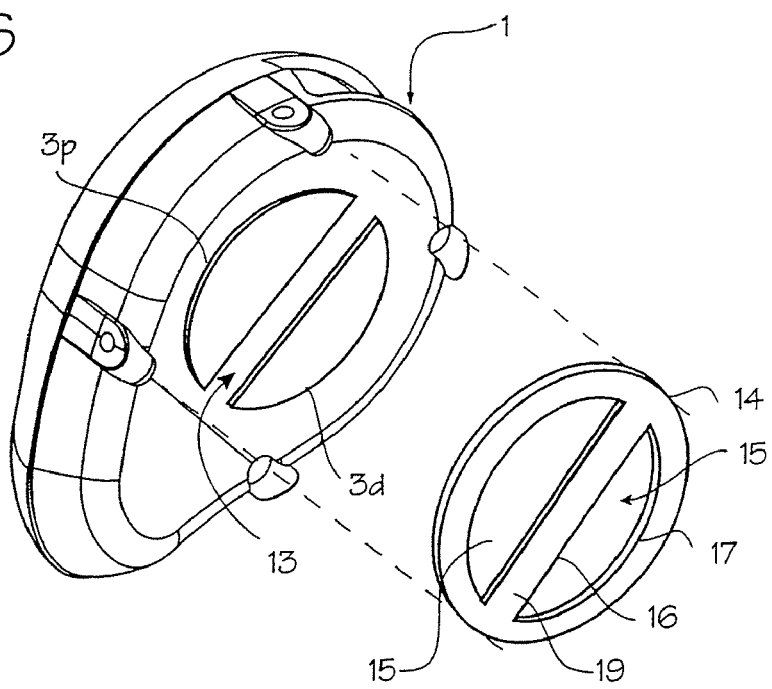
FIG. 6 is an exploded view of the gasket of FIG. 5 adapted to the nerve stimulation device.
Figure 7:
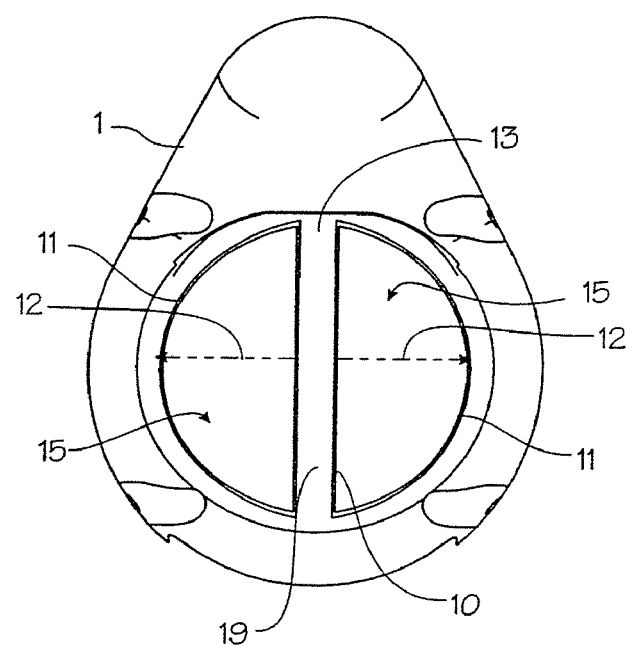
FIG. 7 is a bottom view of the gasket applied to the nerve stimulation device.

FIG. 6 is an exploded perspective view of the gasket 14 applied to the nerve stimulation device 1. FIG. 7 is a bottom view of the gasket applied to the nerve stimulation device. The gasket is applied to the device such that the apertures 15 are fitted over the electrodes, with the electrode-separating member 19 disposed within the inter-electrode gap 13. When the electrode-separating member is applied to the device, the member acts as an insulator between the two electrodes to prevent a short circuit between the electrodes. The electrode-separating member prevents the possibility of conductive materials, such as perspiration or ambient water, from lodging within the inter-electrode gap and causing a short between the electrodes while the device is in use. The nerve stimulation device 1 can be manufactured with the gasket 14 formed integral with the device. Alternatively, the gasket can be a separate component such that the gasket can be detached from the device and be replaced.

Figure 8:
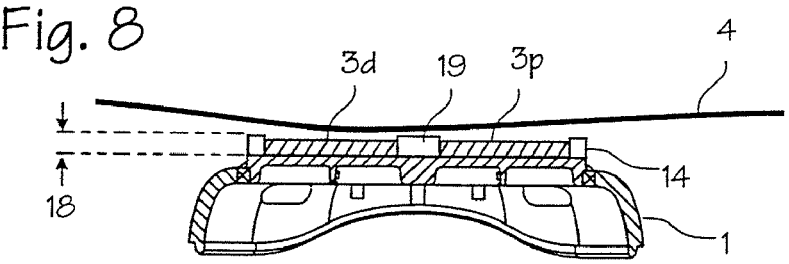
FIG. 8 is a cross-sectional view of the gasket and the nerve stimulation device secured to the patient's wrist.

FIG. 8 shows a cross-sectional view of the gasket 14 and the nerve-stimulation device 1 in use on the patient's wrist. Since the watch housing is secured to the wrist with a band which may be tightened about the wrist, or with an elastic band, some compression of the gasket is expected. The gasket should have sufficient thickness 18 such that when the gasket is applied to the device, the gasket is thick enough when applied to the body to extend from the housing to the skin, and should not be so thick after compression that contact between the electrodes and the skin is impeded. This permits proper-contact between the electrodes and the patient's wrist 4 to provide sufficient nerve stimulation about the P6 point. This condition is easily met with a gasket made of neoprene if the neoprene thickness (uncompressed) is slightly greater than the electrode depth, and the inner surface of the neoprene (uncompressed) is slightly higher than the surface of the electrodes. For stiffer materials, the thickness (uncompressed) may be substantially the same as the electrode depth, and the inner surface of the gasket may be substantially co-planar with the surface of the electrodes. When applied to the wrist the gasket acts as an electrical insulator between the electrodes (as described above) and as a seal between the electrodes and the patient. The gasket seals in any perspiration that may develop between the electrodes and the wrist to enhance the electrical conduction to the wrist.

In use, the gasket is placed over the inside of the housing so that the electrodes are disposed within the apertures. The user may then apply the device to the wrist with or without application of conductivity gel. The device is secured over an acupuncture point, and gently held against the skin, urged or biased toward the skin with light force exerted by the band. The device is then operated to generate an electrical pulse pattern with a 350 microsecond pulse width at about 31 pulses per second at power levels of about 10-35 milliamps peak pulse height. This pulse pattern is effective to create an electro-acupuncture effect on the nerve, but other pulse patterns may also be effective. The user will feel the same effect as application of the same stimulus through oblong electrodes and conductivity gel. Additionally, the user may apply gel, and the device may be programmed to generate pulses at lower power levels, thereby conserving battery life. With the gasket in place, the user may wear the device in a wet environment, and the electrodes will be isolated. The gasket may be used in conjunction with electro-acupuncture devices, TENS devices, and other nerve stimulation devices to protect the devices from environmental contaminants and to enhance the conductive contact between the electrodes and the skin.

While the preferred embodiments of the devices and methods have been described in reference to the environment in which they were developed, they are merely illustrative of the principles of the inventions. Other embodiments and configurations may be devised without departing from the spirit of the inventions and the scope of the appended claims.

What is claimed is:

1. A nerve stimulation device for applying electrical stimulation to a nerve in a patient, through the skin of the patient, the course of said nerve establishing a line along the patient's body, said device comprising:
    a housing adapted for application to the body of the patient over the nerve, said housing having a bottom outer surface for application to the skin of the patient;
    a pair of exposed metal electrodes attached to the bottom outer surface of the housing;
    a band attached to the housing, said band adapted to secure the housing to the body, said band arranged relative to the housing and the electrodes such that, when the housing is secured to the body, the electrodes are positioned to directly contact the skin of the patient and are disposed longitudinally along the line established by the nerve;
    pulse generating circuitry housed within the housing, said pulse generating circuitry operably connected to the electrodes to provide electrical pulses to the nerve through the electrodes;
    a gasket having a first aperture and a second aperture being sized and dimensioned to receive the electrodes, said gasket disposed about the electrodes on the bottom outer surface of the housing; and
    wherein the electrodes extend a given depth outwardly from the bottom outer surface of the housing, and the gasket is a compressible electrically insulating gasket having a thickness in an uncompressed state which is greater than the given depth of the electrodes and a thickness in a compressed state which does not impede direct contact between the electrodes and the patient.

2. The device of claim 1, wherein the gasket comprises neoprene.

3. The device of claim 1, wherein the gasket comprises silicone.

4. The device of claim 1, wherein the gasket includes an electrode-separating member extending between the first and second apertures to electrically isolate the electrodes from one another.

5. The device of claim 4, wherein the electrode-separating member extends substantially perpendicularly to the line established by the nerve when the housing is secured to the body.

6. The device of claim 1, wherein when the housing is secured to the wrist of the patient, the exposed bottom outer surface of the electrodes directly contacts the body of the patient without a layer of conductivity gel intervening therebetween.

7. An electro-acupuncture device for applying electro-acupuncture stimulation to a nerve in a patient, through the skin of the patient, the course of said nerve establishing a line along the patient's body, said device comprising:
    a housing adapted for application to the body of the patient over the nerve, said housing having a bottom outer surface for application to the skin of the patient;
    a pair of metal electrodes attached to the bottom outer surface of the housing, said electrodes each having an exposed bottom outer surface adapted for direct contact with the skin of the patient;
    pulse generating circuitry housed within the housing, said pulse generating circuitry operably connected to the electrodes to provide electrical pulses to the nerve through the electrodes, said pulse generating circuitry providing said electrical pulses in a pulse pattern effective to create an electro-acupuncture effect on the nerve;

a band attached to the housing, said band adapted to secure the housing to the body, said band arranged relative to the housing and the electrodes such that, when the housing is secured to the body, the electrodes are positioned to directly contact the skin of the patient and are disposed longitudinally along the line established by the nerve;

a gasket having a first aperture and a second aperture, said first and second apertures being sized and dimensioned to receive the electrodes, said gasket disposed about the electrodes on the bottom outer surface of the housing; and wherein the electrodes extend a given depth outwardly from the bottom outer surface of the housing, and the gasket is a compressible electrically insulating gasket having a thickness in an uncompressed state which is greater than the given depth of the electrodes and a thickness in a compressed state which does not impede direct contact between the electrodes and the patient.

8. The device of claim 7, wherein the gasket comprises neoprene.

9. The device of claim 7, wherein the gasket comprises silicone.

10. The device of claim 7, wherein the gasket includes an electrode-separating member extending between the first and second apertures to electrically isolate the electrodes from one another.

11. The device of claim 10, wherein the electrode-separating member extends substantially perpendicularly to the line established by the nerve when the housing is secured to the body.

12. The device of claim 7, wherein when the housing is secured to the wrist of the patient, the exposed bottom outer surface of the electrodes directly contacts the inside of the wrist of the patient without a layer of conductivity gel intervening therebetween.

13. An electro-acupuncture device for applying electro-acupuncture stimulation to the P6 acupuncture point on the wrist of a patient, said device comprising:

a housing adapted for application to the inside of the wrist of a patient over the P6 acupuncture point, said housing having a bottom outer surface for application to the wrist;

a pair of metal electrodes attached to the bottom outer surface of the housing, arranged such that, when applied to the wrist, one of said electrodes is located distally on the housing, relative to the wrist, and the other of said electrodes is located proximally on the housing, relative to the wrist, said electrodes each having an exposed bottom surface adapted for direct contact with the wrist of the patient;

pulse generating circuitry housed within the housing, said pulse generating circuitry operably connected to the electrodes to provide electrical pulses to the wrist through the electrodes, said pulse generating circuitry providing electrical pulses in a pulse pattern effective to create an electro-acupuncture effect on the P6 acupuncture point;

a gasket having a first aperture and a second aperture, said first and second apertures being sized and dimensioned to receive the electrodes, said gasket disposed about the electrodes on the bottom outer surface of the housing; and wherein the electrodes extend a given depth outwardly from the bottom outer surface of the housing, and the gasket is a compressible electrically insulating gasket having a thickness in an uncompressed state which is greater than the given depth of the electrodes and a thickness in a compressed state which does not impede direct contact between the electrodes and the patient.

14. The device of claim 13, further comprising a band attached to the housing, said band adapted to secure the housing to the wrist of the patient, said band arranged relative to the housing and the electrodes such that, when the housing is secured to the wrist of the patient, the exposed bottom outer surface of the electrodes directly contacts the inside of the wrist of the patient without a layer of conductivity gel intervening therebetween.

15. The device of claim 13, wherein the gasket comprises neoprene.

16. The device of claim 13, wherein the gasket comprises silicone.

17. The device of claim 13, wherein the gasket includes an electrode-separating member extending between the first and second apertures to electrically isolate the electrodes from one another.

* * * * *